(12) United States Patent
Shachor

(10) Patent No.: US 7,502,891 B2
(45) Date of Patent: Mar. 10, 2009

(54) STORAGE MANAGEMENT BASED ON WORKLIST

(75) Inventor: Gal Shachor, Yokneam (IL)

(73) Assignee: International Business Machines Corporation, Armonk, NY (US)

( * ) Notice: Subject to any disclaimer, the term of this patent is extended or adjusted under 35 U.S.C. 154(b) by 178 days.

(21) Appl. No.: 10/697,183

(22) Filed: Oct. 30, 2003

(65) Prior Publication Data

US 2005/0096942 A1    May 5, 2005

(51) Int. Cl.
- *G06F 12/00* (2006.01)
- *G06F 13/00* (2006.01)
- *G06F 13/28* (2006.01)
- *G06F 17/30* (2006.01)
- *G06Q 10/00* (2006.01)
- *G06Q 50/00* (2006.01)

(52) U.S. Cl. .................. 711/137; 711/113; 711/118; 711/135; 711/141; 711/154; 711/161; 711/162; 711/170; 711/171; 711/172; 711/173; 707/200; 707/203; 707/204; 705/2

(58) Field of Classification Search ............... 711/113, 711/118, 135, 141, 154, 161–162, 170–173, 711/137; 707/10, 3, 200, 203–204; 705/2
See application file for complete search history.

(56) References Cited

U.S. PATENT DOCUMENTS

| | | | | |
|---|---|---|---|---|
| 6,247,094 B1 * | 6/2001 | Kumar et al. | ................... | 711/3 |
| 6,260,021 B1 * | 7/2001 | Wong et al. | ..................... | 705/2 |
| 6,349,373 B2 * | 2/2002 | Sitka et al. | ................... | 711/161 |
| 6,574,629 B1 * | 6/2003 | Cooke et al. | .................. | 707/10 |
| 6,574,742 B1 * | 6/2003 | Jamroga et al. | ............. | 713/400 |
| 6,640,244 B1 * | 10/2003 | Bowman-Amuah | ......... | 709/207 |
| 6,671,424 B1 * | 12/2003 | Skoll et al. | .................. | 382/305 |
| 6,910,106 B2 * | 6/2005 | Sechrest et al. | ............. | 711/136 |
| 6,954,767 B1 * | 10/2005 | Kanada | ...................... | 707/204 |
| 2001/0011336 A1 * | 8/2001 | Sitka et al. | ................... | 711/161 |
| 2002/0016718 A1 * | 2/2002 | Rothschild et al. | ............. | 705/2 |
| 2002/0023067 A1 * | 2/2002 | Garland et al. | ................. | 707/1 |
| 2002/0091765 A1 * | 7/2002 | Bocionek | .................... | 709/203 |
| 2002/0152231 A1 * | 10/2002 | Silva-Craig et al. | ......... | 707/204 |
| 2002/0188707 A1 * | 12/2002 | Terrill | ........................ | 709/223 |
| 2004/0071038 A1 * | 4/2004 | Sterritt | ....................... | 365/232 |
| 2004/0243579 A1 * | 12/2004 | Birkhoelzer et al. | ........... | 707/9 |

OTHER PUBLICATIONS

"Digital Imaging and Communications in Medicine" Supplement 10, Basic Worklist Management, 1996.
"The Seven Levels of PACS Integration: a whitepaper" http://www.ringholm.de/docs/02040_en.htm.

* cited by examiner

*Primary Examiner*—Sanjiv Shah
*Assistant Examiner*—Yaima Campos

(57) ABSTRACT

Systems and methods of storage management which are based on a worklist are described. The storage typically although not necessarily includes a faster access part and a slower access part. One of the described methods includes: examining a worklist which schedules at least one modality to perform at least one task; and ensuring that in the faster access part there is available at least some data which based on at least one predetermined rule is deemed likely to be accessed in connection to the at least one task to be performed by the at least one modality scheduled by the worklist. In one application the worklist conforms to a Digital Image Communications in Medicine (DICOM) modality worklist.

11 Claims, 6 Drawing Sheets

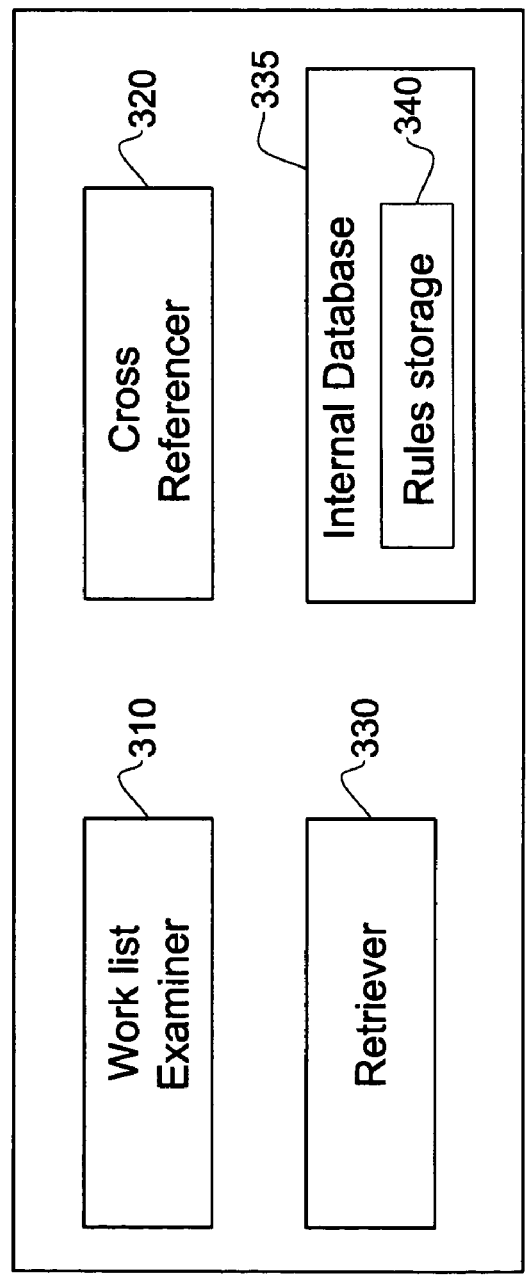

STORAGE MANAGEMENT BASED ON WORKLIST

FIELD AND BACKGROUND OF THE INVENTION

The present invention relates to storage management, including but not exclusively DICOM (Digital Image Communications in Medicine) storage management.

The amount of stored data in a data management system can be large. Therefore a smart storage management technique employs several storage hierarchies, where each of the different storage hierarchies allows for differentiated service in terms of cost, reliability, access time, and bandwidth characteristics. For example, two commonly used storage hierarchies rely on redundant array of inexpensive disks (RAID) and tape devices (for example linear tape open LTO) where the disks allow faster access compared to the tape devices. A key aspect of storage management then becomes the prediction of storage usage and consequently the transfer of data between the different storage hierarchies. Today, most systems cache data (for example in RAID disks) for a fixed amount of time (for example a year) to allow faster access and then place the data in a slower access component of the storage hierarchy (for example on tape). The cache is in a disk, and all references to data being in RAID, are intended to refer to the storage on a RAID disk.

An example of a field where the amount of stored data can be large is the medical field. A medical application such as picture archiving and communication system (PACS) for medical imaging as well as the emerging regulations of the life-long integrated medical records, present storage challenges. Medical imaging systems and clinical healthcare systems need to store large amounts of data for very long periods of time and with a high degree of flexibility. The amount of medical data amassed during a person's lifetime is growing significantly, in part because the new image acquisition machines take advantage of new technologies and produce higher resolution images. The storage consumption of medical imaging is very high and is based on very large objects that are grouped into very large hierarchical data models.

The Health Level 7 (HL7) standard addresses the interfaces among various systems that send or receive patient admissions/registration, discharge or transfer (ADT) data, queries, resource and patient scheduling, orders, results, clinical observations, billing, master file update information, medical records, scheduling, patient referral, and patient care. Some smart medical storage management systems utilize HL7 information such as patient admission and discharge information in order to predict which stored data objects may be required (i.e. predict storage usage). These storage management systems can then transfer those predicted data objects to a faster access storage. However HL7 information is not always available because HL7 is not supported by all hospitals, and even when available, HL7 information is not complete (for example while the HL7 order message may not provide the name of the image acquisition machine assigned to the patient nor the exact time for the procedure, it does provide the procedure's date and patient's details). In addition, because the HL7 information (such as that passed in the HL7 admission message) is of a general nature, prediction of storage usage based on HL7 may result in caching more stored data objects than necessary.

The DICOM standard (version 3.0 was released in 1993) defines a standard method for the transmission of medical images and their associated information, including the specifying of a network protocol utilizing TCP/IP, and the defining of information objects not only for images but also for patients, studies, reports, and other data groupings. The development of the DICOM Standard has permitted the transfer of medical images in a multi-vendor environment, and has also facilitated the development and expansion of PACS and interfacing with medical information systems. DICOM is used or is expected soon to be used by virtually every medical profession that utilizes images within the healthcare industry. These include cardiology, dentistry, endoscopy, mammography, ophthalmology, orthopedics, pathology, pediatrics, radiation therapy, radiology, surgery, etc. DICOM is even used in veterinary medical imaging applications.

Independence from the underlying network technology allows DICOM to be deployed in many functional areas of application, including but not limited to communication within a single site (often using various forms of Ethernet), between sites over leased lines or virtual private networks (VPNs), within a metropolitan area (often using ATM), across dial-up or other remote access connections (such as by modem, ISDN or DSL), and via satellite (with optimized protocol stacks to account for increased latency).

At the DICOM application layer, the services and information objects address five primary areas of functionality:

Transmission and persistence of complete objects (such as images, waveforms and documents), Query and retrieval of such objects, Performance of specifications (such as printing images on film), Workflow management (support of worklists and status information), and Quality and consistency of image appearance (both for display and print).

SUMMARY OF THE INVENTION

It is an object of the invention to provide an improved task scheduler that prefetches what is considered to be relevant data based on the nature of the task or the operative scheduled to perform it.

According to one aspect of the invention there is provided a method of managing a storage, wherein the storage includes a faster access part and a slower access part, comprising:

examining a worklist which schedules at least one modality to perform at least one task; and ensuring that in the faster access part there is available at least some data which based on at least one predetermined rule is deemed likely to be accessed in connection to said at least one task to be performed by said at least one modality scheduled by said worklist.

According to a second aspect of the invention, there is provided a method of managing a medical storage, wherein the storage includes a faster access part and a slower access part, comprising:

querying a Digital Image Communications in Medicine (DICOM) modality worklist service and receiving data related to at least one task which said DICOM modality worklist has scheduled at least one image acquisition machine to perform; and ensuring that in the faster access part there is available at least some data which based on at least one predetermined rule is deemed likely to be accessed in connection to said at least one task which said DICOM modality worklist has scheduled said at least one image acquisition machine to perform.

According to a third aspect of the invention, there is provided a system for storage management, comprising:

at least one modality configured to perform at least one task in accordance with a scheduling by at least one worklist;

a storage configured to store data, including a faster access part and a slower access part; and a prefetcher configured to examine said at least one worklist and configured to ensure that at least some data deemed likely to be accessed in connection to said at least one task is present in said faster access part of said storage.

According to a fourth aspect of the invention, there is provided a system for medical storage management, comprising:

at least one image acquisition machine configured to perform at least one task in accordance with a scheduling by at least one Digital Image Communications in Medicine (DICOM) modality worklist a storage configured to store data, including a faster access part and a slower access part; and a prefetcher configured to examine said at least one worklist and configured to ensure that at least some data deemed likely to be accessed in connection to said at least one task is present in said faster access part of said storage.

According to a fifth aspect of the invention, there is provided a system for prefetching, comprising:

a worklist examiner configured to examine a worklist and determine at least one type of data likely to be accessed, said at least one type of data being related to a task to be performed by a modality scheduled by said worklist;

a cross referencer configured to compare said at least one type of data with data stored for an entity identified for said task; and a retriever configured to transfer or copy data stored for said identified entity which is of at least one of said types and is available only in a slower access part of a storage to a faster access part of said storage.

BRIEF DESCRIPTION OF THE DRAWINGS

The invention is herein described, by way of example only, with reference to the accompanying drawings, wherein:

FIG. 2 illustrates an example of a worklist, in accordance with a preferred embodiment of the present invention;

FIG. 3 illustrates a prefetcher, in accordance with a preferred embodiment of the present invention;

DETAILED DESCRIPTION OF THE INVENTION

A preferred embodiment of the present invention is of systems and methods of storage management which are based on a worklist.

The principles and operation of storage management according to the present invention may be better understood with reference to the drawings and the accompanying description. All examples given below are non-limiting illustrations of the invention described and defined herein.

Figure 1:
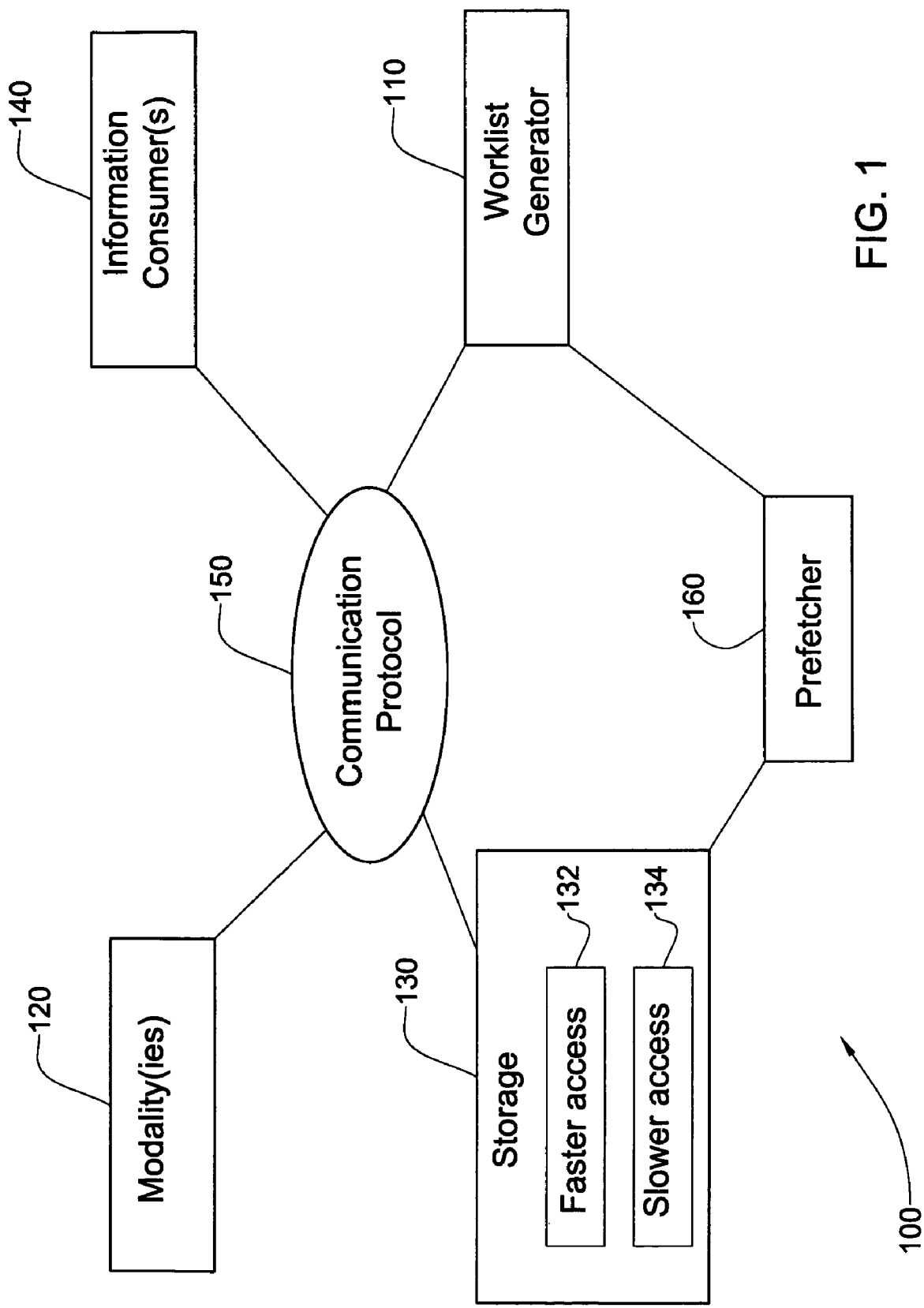
FIG. 1 is a block diagram of a system which includes storage management in accordance with a preferred embodiment of the present invention.

Referring now to the drawings, FIG. 1 illustrates a system 100, in accordance with a preferred embodiment of the present invention. Depending on the embodiment, the illustrated components of system 100 can be concentrated in one physical location or distributed over a geographical area.

The term "data" or "information" as used below refers to data/information in any format, for example text, image, sound, or any other format, as long as the format used is capable of conveying knowledge to the receiver(s) of the data/information.

It is assumed in the following description that data located in a storage 130 can be located in a faster access part 132 of storage 130, in a slower access part 134 of storage 130 or in both parts 132 and 134. The faster access part 132 and slower access part 134 can for example be considered to be storage hierarchies of storage 130. However, this is not mandatory and there may be applications where data is located in only one part 132 or 134 of storage 130 at a time.

Depending on the embodiment, storage 130 can include any combination of suitable storage media. For example, storage 130 can include (faster access) disks 132 and (slower access) tapes 134. As another example, storage 130 can include data stored in a more accessible area 132, for example a closer file cabinet, closer computer, etc. and data stored in a less accessible area 134, for example a more distant file cabinet, more distant computer, etc. Although storage 130 is illustrated as one element and is referred herein in the singular, it should be evident that storage 130 can be concentrated in one physical location or distributed over different physical locations. It should also be evident that each of faster access storage part 132 and/or slower access storage part 134 is not necessarily uniform and that faster access storage part 132 and/or slower access storage part 132 may each comprise a single storage medium or a combination of storage media, and that each may be concentrated in one physical location or may be dispersed over different physical locations.

Typically although not necessarily storage 130 is associated with a storage management application. For example, using criteria such as age, size, name, type, location, and/or any other characteristic of particular data, occupancy level of faster access part 132, availability of media, access to slower access part 134, etc., an associated storage management application may decide if and when to copy particular data from faster access storage part 132 to slower access storage part 134.

The storage management application may for example cause particular data to be immediately purged from faster access part 132 after having been copied to slower access part 132 (effectively executing a transfer of the particular data) or as another example may allow the data which has already been copied to be deleted whenever more space in faster access part 132 is needed.

A worklist generator 110 assigns tasks to one or more modalities 120. Worklist generator 110 is defined herein as an element which is configured to generate a worklist and can therefore be any combination of software, hardware and/or firmware, or alternatively a human that performs the functions as defined and explained herein. Modality 120 is defined herein as an element which is configured to perform a task assigned by the worklist and can therefore be any combination of software, hardware and/or firmware, or alternatively a human that performs the functions as defined and explained herein. Although for the sake of simplicity worklist generator 110 is illustrated in FIG. 1 and described below as a single element, in other embodiments there may be multiple worklist generators 110. For example in an embodiment with multiple worklist generators 110, each worklist generator 110 may be associated with (and in some cases even be part of) one or more modalities 120, generating worklists for the associated modalit(ies) 120. For the sake of simplicity, it is also assumed in the description below that each task is a stand-alone task that is assigned to only one modality 120. However in other embodiments, a task can be part of a series of tasks (for example, one step in a procedure). In these other embodiments, different tasks in the series of tasks may in some cases be assigned to different modalities 120. A prefetcher 160 examines the worklist generated by worklist generator 110 and ensures that relevant data related to the tasks assigned to one or more modalities 120 is located in faster access storage part 132 of storage 130. The invention likewise contemplates the situation where a copy of the relevant data is or is not also located at the same time in slower access storage part 134. If any of the relevant data is instead located only in slower access storage part 134 of storage 130, prefetcher 160 transfers or alternatively copies that data to faster access storage part 132. Within the context of the present invention, transferring implies that the data no longer remains in slower access storage part 134, whereas copying implies that a copy of the data remains in slower access storage part 134. Although both copying and transferring are valid embodiments, it should be evident that copying eliminates the need to later transfer back data to slower access storage part 134.

Data that is available in faster access storage part 132 can be more quickly accessed by one or more information consumers 140 than data only available in slower access storage part 134. Information consumer(s) 140 are those person(s) and/or inanimate object(s) who in connection to the assigned task (for example, while preparing for, performing, supervising and/or reviewing an assigned task) may want or need to access data related to the assigned task. Depending on the embodiment, information consumer(s) 140 for a particular task can be any combination of assigned modality 120, the operator of assigned modality 120 and/or one or more third parties. Information consumers 140 can be designated by names and/or by types/groupings. Worklist generator(s) 110, modalit(ies) 120, storage 130, and information consumer(s) communicate using communication protocol(s) 150 appropriate for system 100.

FIG. 2 shows an example of a worklist 200 generated by worklist generator 110, according to a preferred embodiment of the present invention. As mentioned above it is assumed that there is one worklist generator 110 for all modalities 120 in system 100 and therefore an assignment column 210 in worklist 200 lists the type and/or name of the assigned modality 120 for each task. In an embodiment where each modality 120 has an associated worklist generator 110 and therefore a separate worklist 200, column 210 can be omitted. It is assumed in the illustrated embodiment that each task can be assigned to only one modality 120. However in an embodiment where a task can be assigned to more than one modality 120, all assigned modalities 120 can be listed in column 210 for each task.

A scheduling column 220 provides scheduling information, for example depending on the embodiment, the time of task assignment, the scheduled time for task execution, the placement of a task within an execution sequence of some or all of the tasks assigned to a particular modality 120, the placement of a task assigned to a particular modality 120 within an execution sequence of a series of tasks assigned to more than one modality 120, and/or any other relevant scheduling information which allows a particular modality 120 to carry out assigned tasks in a timely manner. In the illustrated example of FIG. 2, the time of task assignment is shown in column 220. If in a particular embodiment, scheduling is not required (for example if in a particular system 100 modalities 120 can choose the order of performing tasks), then scheduling column 220 can be omitted.

A task description column 230 describes the assigned task. In some embodiments, task description column 230 may be omitted in worklist 200 (or alternatively ignored by prefetcher 160), for example if the type or name of modality 120 (included in column 210) inherently describes the task. Inherent description may arise for example if modality 120 specializes in performing one task. Specialized modality 120 can be a person specializing in one task such as a heart-transplant surgeon, an air-conditioner repair person, etc. or a machine specializing in one task such as a photocopier, mammography scanner etc.

An identification column 240 identifies the entity (for example individual, family, animal, corporation, organization, inanimate object, etc.) on whom or for whom the task will be performed. Identification column 240 can include the name, personal identification number such as social security number, address, email address, phone/fax number, and/or any other information which identifies the entity. In some systems 100 columns 230 and 240 may be combined together.

An optional information consumer column 250 lists the expected information consumer(s) 140 of any relevant data that is related to the assigned tasks. Column 250 can list names of expected consumers 140 (for example Dr. Smith) and/or a grouping/type describing expected consumers 140 (for example radiation oncologist). In other embodiments, worklist 200 does not have a separate column 250 listing expected consumers 140, but worklist 200 lists other information such as for example the referring agent (for example physician or other medical staff, dispatcher, etc.) the performing agent (for example medical staff, technician, etc.), the supervisor, the operator of modality 120, etc., which prefetcher 160 uses as equivalent information to designate information consumers 140. In some embodiments, the assigned modalities 120 listed in column 210 and/or operators of these modalities 120 (even if the name of the operator is not listed in worklist 200) may routinely be designated by prefetcher 160 as information consumers 140.

An optional status column 260 lists the status of the task, for example open (other equivalent terms including outstanding, scheduled, not completed), completed, cancelled, priority, etc. In some cases, the status may be updated based on data received from other parts of system 100, for example from modalities 120.

In the illustrated embodiment it is assumed as mentioned above that each task is a stand-alone task. However in an embodiment where tasks can be part of a series of tasks, all the tasks in a series, along with the assigned modality 120 for each task in the series, may be associated with one another as well as with any common information such as for example information in columns 240 and/or 250.

It should be evident that worklist 200 may have data arranged in a different format than in columns and that the arrangement in columns shown in FIG. 2 is solely for illustration purposes. It should be also evident that in other embodiments, worklist 200 may include more information or less information for a task than shown in FIG. 2.

Prefetcher 160 is defined herein as an element which is configured to examine the generated worklist and ensure that relevant data related to the assigned tasks is located in faster access storage part 132 of storage 130 (whether the relevant data is allowed to also be located at the same time in slower access storage part 134 depends on the particular embodiment). Prefetcher 160 can therefore be any combination of software, hardware, and/or firmware or alternatively a human, that performs the functions as defined and explained herein. In some systems 100 with a storage management application which performs storage management tasks for storage 130, prefetcher 160 can be part of the storage management application. In other systems 100, with or without a storage management application, prefetcher 160 can be a separate element.

"Relevant data" (also termed in the description "relevant information") is defined herein as data related to an assigned task which is stored in storage 130 and which is considered likely to be accessed by information consumer(s) 140 based on predetermined rules. The threshold for likelihood can vary depending on the particular system 100 and can even vary within the same system 100 depending on, for example, the characteristics of the data. Preferably, the rules set a high probability threshold for likelihood so that data which is peripherally related to an assigned task and for which there is only a small probability that information consumer(s) 140 will want access, is not considered likely to be accessed and is not transferred or copied to faster-access storage part 132. In this manner, unnecessary overloading of faster-access storage part 132 is avoided.

FIG. 3 shows an example of the components of prefetcher 160, according to a preferred embodiment of the present invention. A worklist examiner 310 examines the generated worklist, for example the worklist 200 as described above with reference to FIG. 2. In one preferred embodiment, examiner 310 periodically examines the worklist and each time a new scheduled task is recognized (for example a new row in worklist 200), some or all of the data listed for the new scheduled task is saved to an internal database 335. The frequency that examiner 310 examines the worklist can vary depending on the type of system 100 and can also vary for a particular system 100, for example depending on the time of day the frequency may be faster or slower. Alternatively, whenever the worklist changes, the worklist 200 may itself notify the worklist examiner 310.

In the embodiment illustrated in FIG. 3, using predetermined rules stored in a rules storage 340, worklist examiner 310 determines the type(s) of data which information consumers are likely to access for a particular task. In one embodiment, the type(s) of data determined by worklist examiner 310 using the rules, depend primarily on the task described in task column 230. In another embodiment, the type(s) of data determined by worklist examiner 310, using the rules, depend primarily on the task described in or derived from other parts of worklist 200, for example from the name and/or type of assigned modality 120. In some cases, the type(s) of data determined by examiner 310 may be suitable for generic information consumers 140. In other cases the type(s) of data may be tailored to the actual expected consumers 140. The actual expected consumers 140 may be designated by examiner 310 through examination of information consumer column 250 (if available), through examination of other information in worklist 200 such as for example modality column 210 other information in FIG. 2 or other information not shown in FIG. 2, and/or through derivation (for example in some cases the modality 120 and/or operator of modality 120 are routinely designated as one of information consumers 140). In order to tailor the type(s) of data to actual expected consumers 140, rules for those expected consumers 140 would typically although not necessarily have been previously determined and stored in rule storage 340. In some cases, the rules used by worklist examiner 310 may also take into account the values of other columns of worklist 200 to determine types of data which consumers 140 are likely to access. For example a priority status in column 260 may signal that certain types of data should be quickly accessible. As another example, a day-time hour in scheduling column 220 may signal different types of data to be quickly accessible compared to a night-time hour.

Because in the illustrated embodiment the rules used by worklist examiner 310 are assumed to be independent of the identified entity (for example the entity identified through identification column 240), the type(s) of data determined by the rules in the illustrated embodiment are typically although not necessarily pertinent to more than one entity. Therefore in the illustrated preferred embodiment, the term "type(s) of data" refers to class(es) or categori(es) of data which are typically although not necessarily pertinent to more than one entity. For example, computed axial tomography (CAT) scans could be a type of data in system 100. As another example, Honda Civic engine repairs could be a defined type of data. Honda is a trademark of Honda Motor Co., Ltd.

As another example, reference material could be a defined type of data. All of these examples of types of data are typically although not necessarily pertinent to more than one entity.

In the illustrated embodiment, the data-type is typically although not necessarily defined so as to facilitate a correct association with one or more particular tasks. The data-type however may still be defined broadly or narrowly. For example a type of data can be hand X-rays (broader definition) or thumb X-rays (narrower definition).

A cross referencer 320 compares the type(s) of data determined by examiner 310 to be likely to be accessed with the data actually stored in slower-access storage 134 for the identified entity or stored in slower access storage 134 as general reference material. Any data for the identified entity or any general reference material which correspond to the determined type(s) of data and which is stored only in slower access storage 134 (i.e. is not stored in faster access storage 132) is then transferred or copied by a retriever 330 to faster-access storage 132.

Alternatively, cross referencer 320 may compare the types of data determined by examiner 310 to be likely to be accessed with the data actually stored in any part of storage 130 for the identified entity, or stored as general reference material in storage 130. In this alternative embodiment some or all of the types of data which were determined by examiner 310 to be likely to be accessed but are not available in storage 130 for the entity identified in column 240, or not stored in storage 130 as general reference material, may be noted, for example for follow-up (i.e. can any missing data be acquired from another source, etc). Any data for the identified entity or any general reference material which correspond to the determined type(s) of data and which is stored only in slower access storage 134 (and is not stored in faster access storage 132) is then transferred or copied by retriever 330 to faster-access storage 132.

In some cases, retriever 330 may use scheduling information 220 to better manage any transfer or copying of data to faster access storage 132. For example, if scheduling information 220 shows that a task is only scheduled for a later date, retriever 330 may in some cases postpone the transfer or copying of data to a time closer to the scheduled date.

It should be noted that retriever 330 is configured to transfer or copy data between the parts of storage 130 which are differentiated by access time. Therefore the configuration of retriever 330 may vary depending on the particular configuration of storage 130.

In one embodiment, if examiner 310 determines that a scheduled task is cancelled (for example being denoted "cancelled" in column 260), the prefetching process is cancelled. Depending on when the cancellation occurs, the determination of types of data likely to be accessed, the cross-referencing or the retrieving are interrupted. If the cancellation occurs after the retrieval has occurred, the retrieval may be reversed (i.e the transferred or copied data may be transferred back to slower access storage 134 or deleted from faster access storage 132). The transfer back or deletion may be triggered by the determination of cancellation. Alternatively, the transferred or copied data may be marked as "not needed" so the data can be transferred back or deleted based on storage management criteria described above, for example when more space is needed in faster access storage part 132. In other embodiments, examiner 310 may not check for cancellation of scheduled tasks or may not cancel or reverse the prefetching once the prefetching has begun.

It should be evident that the prefetcher components shown in FIG. 3 represent one possible embodiment. In addition, the description of the prefetching process above is one of many possibilities for the illustrated embodiment. In other embodiments, prefetcher 160 can include fewer components, more components, or the same number but different components as long as the functionality of prefetcher 160 can be performed by the totality of the components of the particular embodiment. The description of the prefetching process for other embodiments would be modified accordingly to conform to the components of a particular embodiment.

Depending on the embodiment, data which was transferred or copied from slower access part 134 to faster access part 132 because of predicted likely access by information consumer(s) 140 may or may not be transferred back to slower access part 134 or may or may not be deleted from faster access part 132, once information consumer(s) 140 are no longer predicted to be likely to access the data. In one embodiment for example, once the task has been completed, the data may be transferred back to slower access part 134 or deleted, for example after a constant, system-dependent, task-dependent and/or data-dependent time lag from task completion. In another embodiment, the data may be transferred back to slower access part 134 or deleted based on criteria not directly dependent on task completion, for example after a timeout, such as a time lag from task scheduling (such as 24 hours, end of day, etc), after a patient is discharged from the hospital, etc. In another embodiment, the data may remain in faster access part 132 until the storage management application decides to transfer or copy the data to slower access part 134 or delete the data, based on storage management criteria described above, for example when more space is needed in faster access storage part 132.

Figure 4:
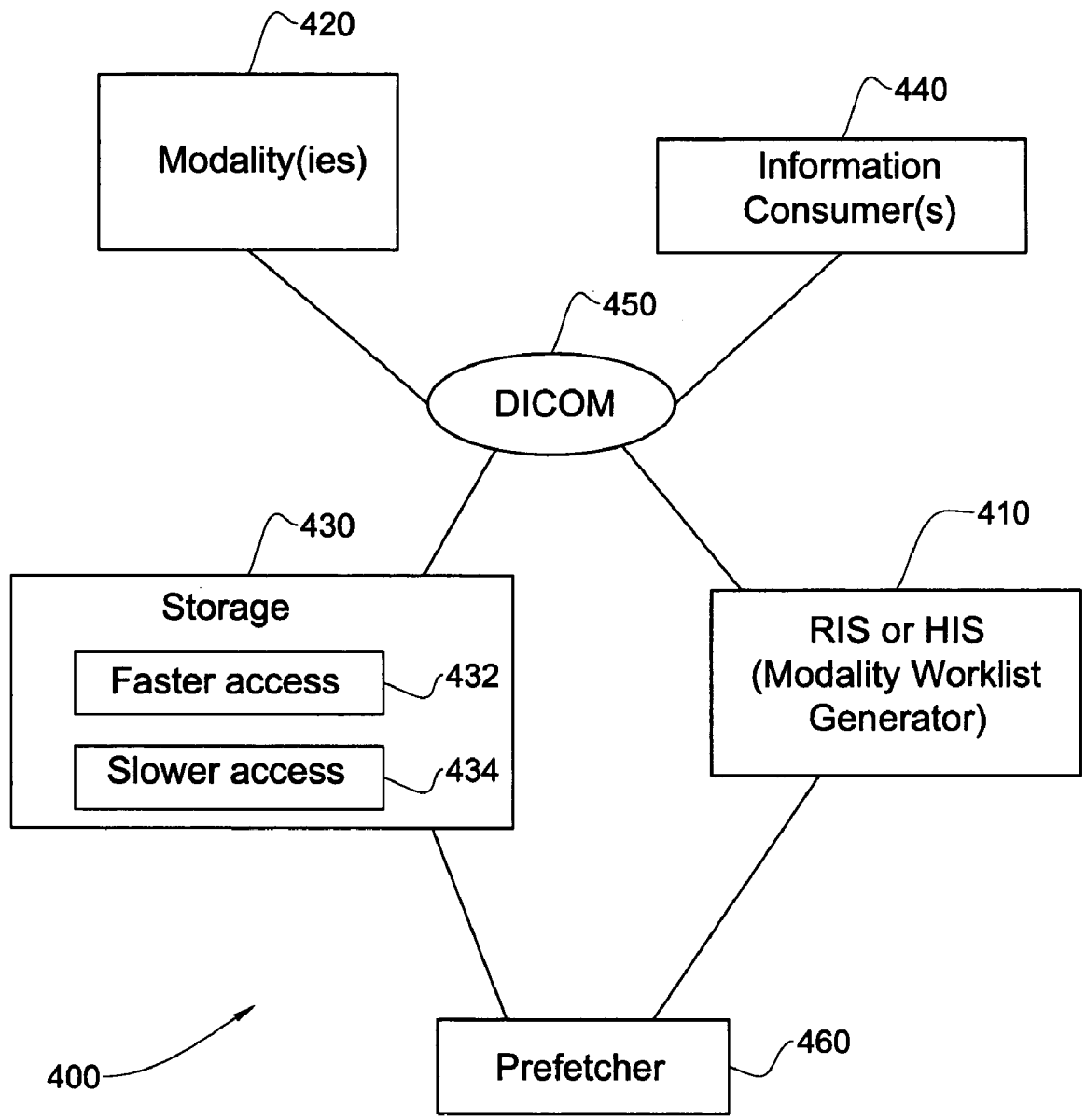
FIG. 4 is a block diagram of a medical system which includes storage management in accordance with a preferred embodiment of the present invention.

FIG. 4 illustrates a medical system 400, according to a preferred embodiment of the current invention. A radiology information system RIS 410 or alternatively a hospital information system HIS 410 functions as the information system for radiology or hospital patients and as the worklist generator. In system 400, the modalities are image acquisition machines 420, for example x-ray machines, magnetic resonance imaging (MRIs), computed tomography (CTs), ECG etc. In the dicom system, the modalities can be things other than image acquisition machines, such as ECG. The modality is a Service Class User (SCU), which is DICOM terminology for a client entity. The information consumer(s) 440 in system 400 can be for example the image acquisition machines, the operators of the image acquisition machines, hospital or radiology staff, affiliated physician offices, performing physicians, referring physicians etc. Prefetcher 460 and storage 430 are examples of prefetcher 160 and storage 130 respectively, and operate as described above with particular reference to FIGS. 1 and 3 of the drawings. Communication between the different components of system 400 follows the DICOM standard 450.

As mentioned above the DICOM application layer addresses the functionality of workflow management including support of worklists. As such, DICOM defines a basic modality worklist management service. The DICOM worklist which is generated by RIS or HIS 410 describes the assigned tasks for image acquisition machines 420.

Figure 7:
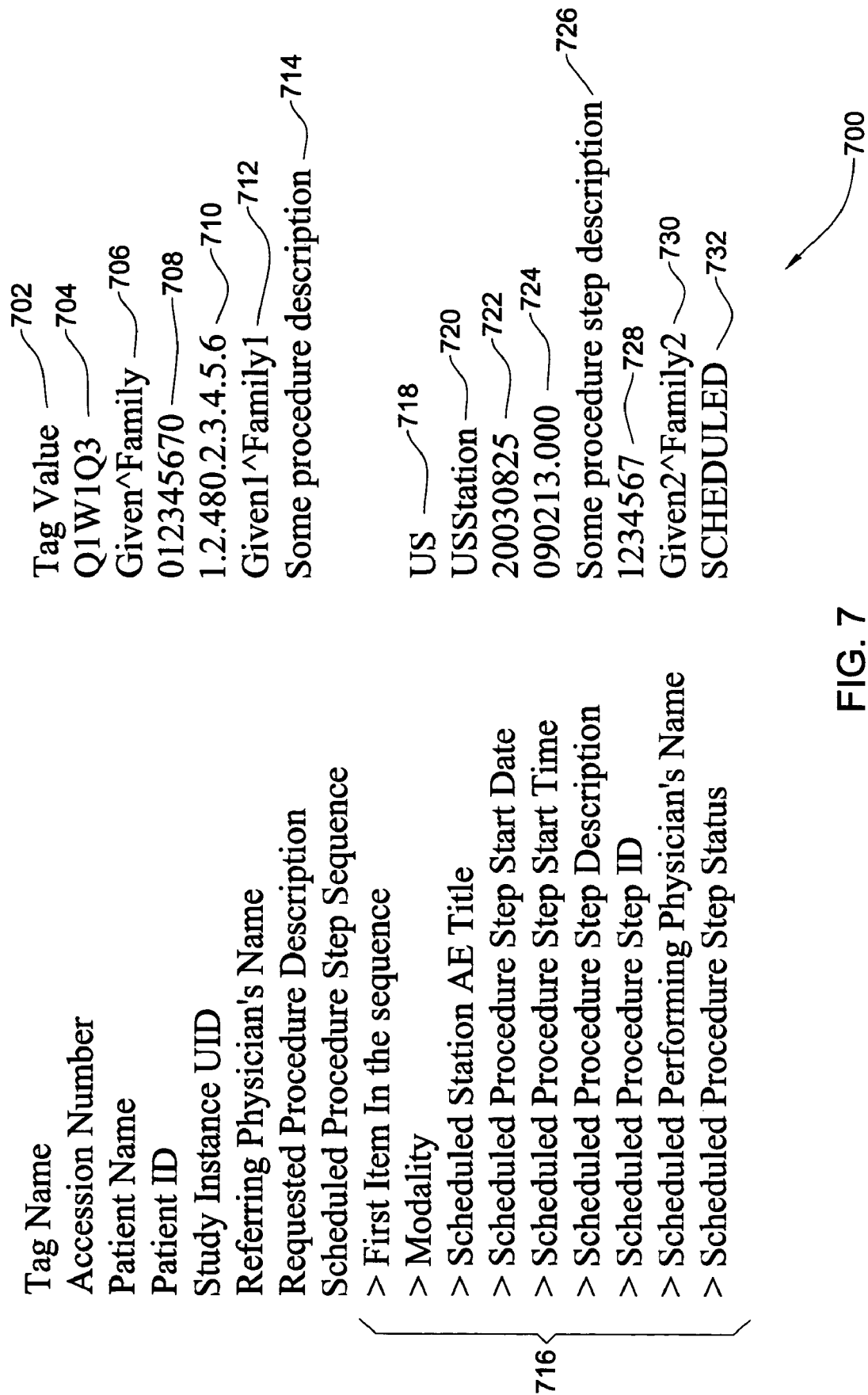
FIG. 7 illustrates an example of a DICOM modality worklist, in accordance with a preferred embodiment of the present invention.

The worklist management service allows elements of system 400 to query the modality worklist generator RIS or HIS 410 and receive the assigned tasks for each modality 420. The rate of querying is configurable and may be the same or different for different elements of system 400. In addition the rate of querying may be the same or may differ for a particular querying element depending on factors such as how busy the querying element is, time of day, etc. The querying entity may be, for example each modality 420, so as to prepare for the expected task. In accordance with the present invention, prefetcher 460 uses the worklist management service to periodically query the worklist for tasks assigned to all modalities 420 and thereby predict storage use. Refer to FIG. 7 which shows an example of a DICOM modality worklist 700, according to a preferred embodiment of the present invention. Worklist 700 can be considered a special format of generic worklist 200, adapted to conform to the DICOM standard. Modality worklist 700 is illustrated for one procedure which in this example is made up of one step (task). (Typically although not necessarily, each step in a procedure can be performed by a different modality 420). The scheduled procedure has an accession number 704 which links the information with the data model used by HIS 410. The scheduled procedure also has a study instance unique identification 708 which links the information with the data model used by PACS (not shown). The patient name 706 and patient ID 708 identify the patient (corresponding to information in column 240 of the generic worklist 200 above). The referring physician name (or name of other referring medical staff such as technician, nurse, etc) 712 and procedure description 714 are also provided. The task (i.e. step) is defined by information 716. Modality 420 is described by both a type 718 and a name 720 (corresponding to information in column 210 of generic worklist 200 above). The start date 722 and start time 724 provide scheduling information for the task (corresponding to information in column 220 of generic worklist 200 above). A description 726 of the task is also provided along with an identification number of the task 728 (corresponding to information in column 230 of generic worklist 200 above). The name of the performing physician (or name of other performing medical staff such as technician, nurse, etc) 730 is shown. The status 732 of the task is also shown (corresponding to information in column 260 of generic worklist 200 above). It should be evident that in other embodiments, worklist 700 can include more, less or different information regarding a procedure.

In one embodiment, prefetcher 460 uses patient name 706, patient ID 708, modality 718, scheduled station AE title tag 720, start date 722, start time 724, referring physician's name 710 and performing physician's name 730 to ensure that relevant data related to the assigned task is located in faster access storage part 432 of storage 430. For example examiner component 310 of prefetcher 460 can examine modality 718 and title tag 720 and thereby determine using predetermined rules the type(s) of data which (generic) information consumers are likely to access for the assigned task. As another example, examiner component 310 may designate referring physician (or other referring medical staff) 712 and/or performing physician (or other performing medical staff) 730 as information consumers 440 and tailor the types of data accordingly. As another example, cross referencer component 320 of prefetcher 460 may use patient name 706 and patient ID 708 to compare the types of data determined by examiner 310 with data actually stored for the identified patient. As another example, retriever component 330 may use start date 722 and/or start time 724 as a deadline for retrieving any relevant data only stored in slower access part 434. In other embodiments, prefetcher 460 may use additional information on worklist 700, less information on worklist 700 and/or different information on worklist 700 to ensure that relevant data related to the assigned task is located in faster access storage part 432 of storage 430.

Figure 5:
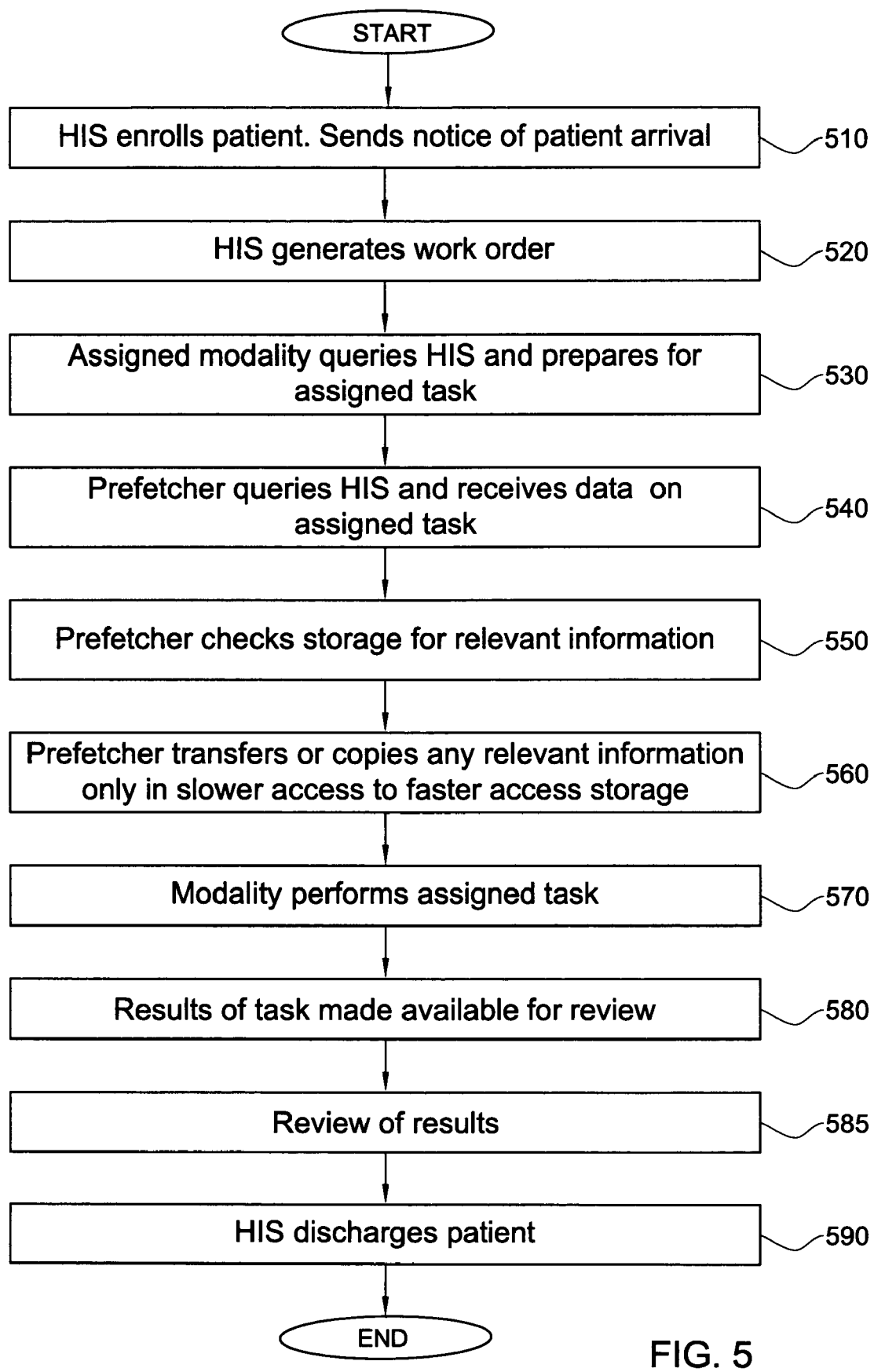
FIG. 5 is a flowchart of a medical pre-fetching method, in accordance with a preferred embodiment of the present invention.

FIG. 5 illustrates a flowchart of a medical pre-fetching method, in accordance with an embodiment of the current invention. The order of stages is for sake of illustration and in other embodiments may be changed. For clarity of explanation, the flowchart follows the path of a typical patient, Ms. Abbot through a hospital visit to the emergency room. In stage 510, Ms. Abbot arrives on Jul. 29, 2003 in her 30$^{th}$ week of pregnancy, complaining that she is not feeling the baby moving. Admitting data on Ms. Abbot is entered into HIS 410. HIS 410 sends a notice to all parts of system 400 that Ms Abbot has arrived.

In stage 520, Ms. Abbot is examined by a gynecologist in the emergency room, Dr. Davidson. Dr. Davidson orders an ultrasound of Ms Abbot's uterus. The ultrasound order is entered into HIS 410 at 10.20 AM, and is scheduled for the same day, ten minutes later. HIS 410 generates a work order for Ms Abbot. For example the work order could resemble the following (assuming the format of sample DICOM modality worklist 700):

| Tag Name | Tag Value |
| --- | --- |
| Accession Number | Q1W1Q3 |
| Patient Name | Shirley Abbot |
| Patient ID | 012345670 |
| Study Instance UID | 1.2.480.2.3.4.5.6 |
| Referring Physician's Name | Stuart Davidson |
| Requested Procedure Description | 30 week pregnancy ultrasound |
| Scheduled Procedure Step Sequence | |
| First Item In the sequence | |
| Modality | US |
| Scheduled Station AE Title | US5 |
| Scheduled Procedure Step Start Date | 20030729 |
| Scheduled Procedure Step Start Time | 10.30 |
| Scheduled Procedure Step Description | 30 week pregnancy ultrasound |
| Scheduled Procedure Step ID | 1234567 |
| Scheduled Performing Technician Name | William Newman |
| Scheduled Procedure Step Status | SCHEDULED |

In stage 530, the assigned image acquisition machine 420, ultrasound 5, queries HIS 410 and prepares for the task.

In stage 540, prefetcher 460 queries HIS 410 and receives data on the assigned task. Optionally, prefetcher 460 stores the received data in internal database 335. Optionally, prefetcher 460 may receive in the same query data on other newly assigned tasks. It should be evident that the order of stages 530 and 540 can be interchanged and the rate of querying by modalities 420 and prefetcher 460 may be the same or may differ from one another.

In this example it is assumed that prefetcher 460 designates as information consumers 440 the referring physician (included in the work-order) as well as the operator of modality 420, i.e. the ultrasound (performing) technician (also included in the work order).

It is also assumed that the rules stored in rule storage 340 for pregnancy ultrasounds state that all available previous ultrasounds for the same pregnancy be accessible in faster access storage 432. It may be determined that the ultrasound relates to a pregnancy ultrasound by examining just modality name (i.e. without step description) by using side information that indicates that the modality is located inside the delivery room/women's emergencies and then deduce that it is used for this task. It is prone to error to trust only the description without further qualifying data. Moreover it is assumed that the rules state that for any non routine ultrasound reference material regarding pregnancy support groups be accessible in faster access storage 432, in case the patient requests the information. Priority can also be inferred from auxiliary information associated with the modality. For example if a certain modality is used within the emergency room, chances are that the priority is high. Priority might also be inferred from the physician's name. It is also assumed that rules for Dr. Davidson state that for any visit of a pregnant patient, Dr. Davidson would like data on hospital visits for previous pregnancies (for example visits for miscarriages, live births, abortions, ultrasounds) for the patient be accessible in faster access storage 432.

It is assumed that the storage management policy is to maintain all data from the past year as well as certain reference data on faster access storage part 432 In stage 550, prefetcher 460 checks storage 430 for previous ultrasounds of Ms. Abbot's current pregnancy, data on visits related to earlier pregnancies of Ms. Abbot, and reference material on support groups. Owing to the assumed storage management policy, the previous ultrasounds of the current pregnancy and the reference material on support groups are already present on faster access storage part 432. However, data on visits related to past pregnancies is assumed to be stored only in slower access storage part 434 and therefore in stage 560, prefetcher 460 transfers or copies that data to faster access storage part 432.

It should be noted that Ms. Abbot had previously visited the hospital for pneumonia, a broken leg, and recurring headaches, and data related to these illnesses is available only in slower access storage 434. However this data is not transferred or copied to faster access storage 432 in stage 560 because it is assumed that based on the predetermined rules it is concluded that it is unlikely that information consumers will want to access data related to those previous visits during this visit. (It should be evident that the rules could have been constructed in a different way that would have required the transfer/copying of this data). Because of the availability of the task description provided by the modality worklist, the rules can be constructed so as to more narrowly define the types of data which information consumers (in our example, Dr. Davidson and W. Newman, the scheduled technician) will be likely to access. Therefore overloading faster access storage part 432 is less likely using the current invention than for a blanket retrieval of all data related to Ms Abbot.

In stage 570, ultrasound machine 5420 takes an ultrasound of Ms. Abbot. During the ultrasound, the operator of ultrasound 420, W. Newman accesses the earlier ultrasounds as baselines. It is assumed that the current ultrasound shows normal movement of the fetus. In stage 580, the ultrasound results are made available for review. Depending on the embodiment, the results may be stored in faster access storage 432 (where the results can be retrieved for example by Dr. Davidson) and/or the results can be explicitly moved to, for example, Dr. Davidson (for example through a DICOM C-Move).

In stage 585, Ms. Abbot is again seen by Dr. Davidson. During his examination of Ms. Abbot, Dr. Davidson accesses the current ultrasound from faster access storage 432. In addition, Dr. Davidson accesses the information about past pregnancies that prefetcher 460 had previously transferred or copied to faster access storage part 432 and notices that Ms. Abbot's previous pregnancies had resulted in normal live births. Due to the positive results of the current ultrasound and previous pregnancies, Dr. Davidson does not access the reference material on support groups. Dr. Davidson enters data on the visit in HIS 410.

In stage 590, discharge information on Ms. Abbot is entered in HIS 410 and HIS 410 sends a notice to all parts of system 400 that Ms. Abbot has been discharged. It is assumed in this example that the information previously transferred or copied to faster access storage part 432 remains there until Ms. Abbot is discharged from the hospital, after which the information is transferred back or deleted.

Figure 6:
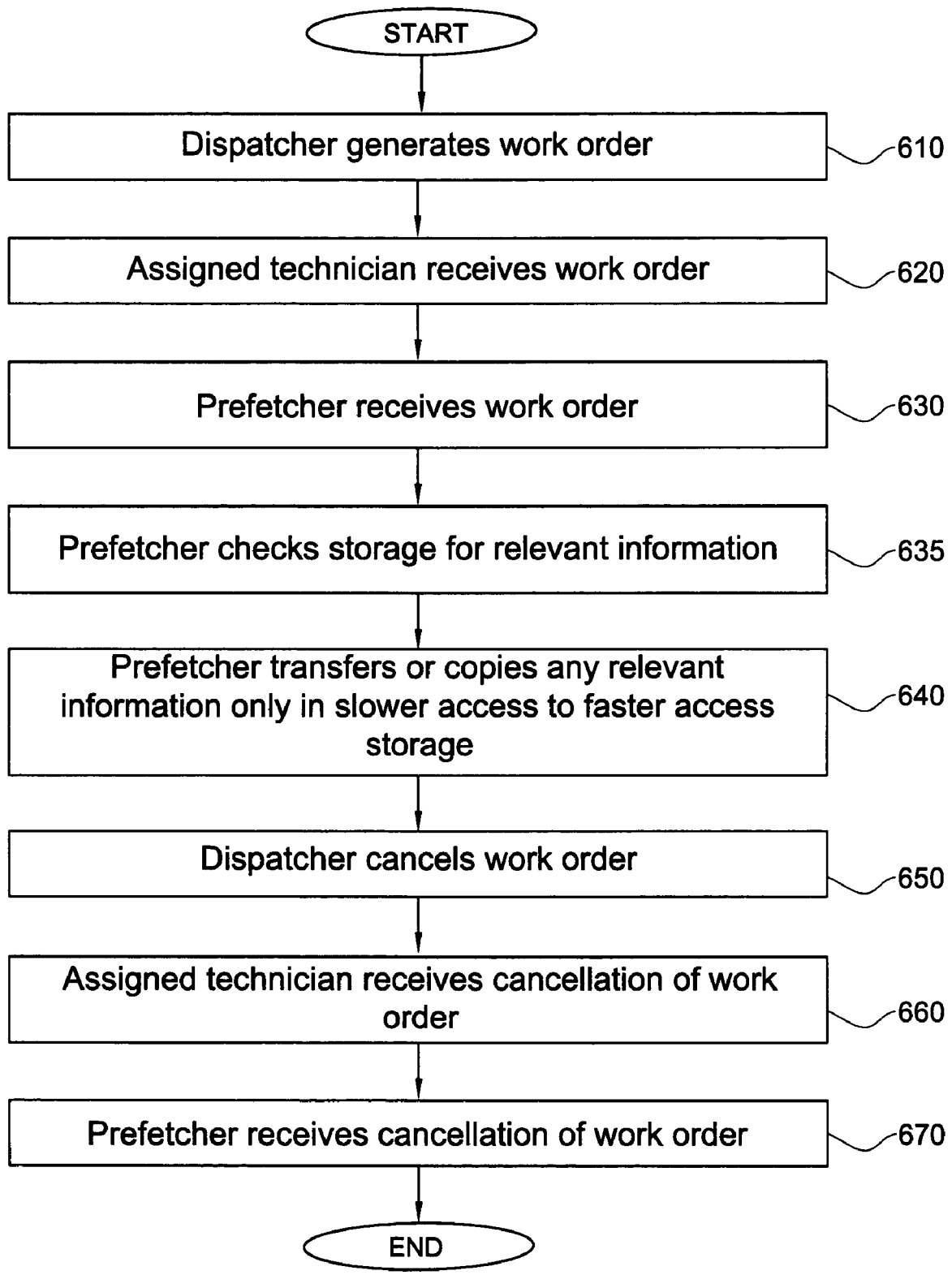
FIG. 6 is a flowchart of another prefetching method, in accordance with a preferred embodiment of the present invention.

FIG. 6 illustrates a flowchart of another prefetching method in accordance with a preferred embodiment of the present invention. The order of stages is for the sake of illustration and in other embodiments the stages may occur in a different order. In this example, a service call is made to a major appliance repair service. One of the burners on the x-brand stand-alone oven of customer S. Kay is not lighting. In stage 610, The dispatcher generates a work order, including for example the name of the scheduled technician, the scheduled time of the visit, the task, the name and address of the customer, the information consumer (here assumed to be scheduled technician whose work-level is trainee technician) and the status of the task. For example, the work order could include the following information (assuming the format of worklist 200):

E. Braham; Tues 3 PM; fix burner, S. Kay 3203 Woodslane; trainee, open

In stage 620, E. Braham receives the work order.

In stage 630, prefetcher 160 receives the work order. In step 635 prefetcher 160 checks storage 130 for relevant data related to the assigned task. For example, assume that the rules state that for a task related to burners, all past problems for the scheduled oven should be in faster access storage 132 as well as data on any known manufacturing defects for burners of the brand of scheduled oven (here x-brand). In addition, assume that E. Braham is part of group of trainee technicians and the rules for trainees state that reference material on how to perform a task (here, how to fix burners) should be in faster access storage 132. Therefore, in stage 640, data on past problems for Mr. Kay's oven, data on manufacturing defects of the x-brand burner, and reference material on fixing burners, all of which is assumed to be stored only on slower access storage 134, is transferred or copied to faster-access storage 132.

Assume that the customer, Mr. Kay later calls and cancels the repair visit. In stage 650, the dispatcher cancels the work order, for example by generating the same work order but with the status cancelled as shown below.

E. Braham; Tues 3 PM; fix burner, S. Kay 3203 Woodslane; trainee, cancel

In stage 660, E. Braham receives notice of cancellation of the work order.

In stage 670, prefetcher 160 receives notice of cancellation of the work order. In this example it is assumed that upon cancellation, prefetcher 160 transfers back to slower access storage 134 (or deletes) any data which in stage 640 was previously transferred (or copied) to faster access storage 132.

It will also be understood that the system according to the invention may be a suitably programmed computer. Likewise, the invention contemplates a computer program product comprising a computer useable medium having computer readable program code embodied therein configured to cause a computer to execute the method of the invention. The invention further contemplates a memory readable by machine tangibly embodying a program of instructions executable by the machine for executing the method of the invention.

While the invention has been described with respect to a limited number of embodiments, it will be appreciated that many variations, modifications and other applications of the invention may be made.

What is claimed is:

1. A method of managing a storage, wherein the storage includes a faster access part and a slower access part, the method comprising:
    periodically querying by a prefetcher, using a Digital Image Communications in Medicine (DICOM) communications protocol, a DICOM modality worklist for information regarding at least one task scheduled to be performed by at least one modality listed in said DICOM modality worklist;
    querying said DICOM modality worklist by said at least one modality, at a configurable query rate, using said DICOM communications protocol, for information regarding at least one task scheduled to be performed by said at least one modality,
    wherein said configurable query rate is based on at least one parameter selected from the group consisting of: time of day, and workload of said at least one modality;
    determining, based on information received by said prefetcher and at least one predetermined rule, at least one type of data likely to be accessed in connection with said at least one task; and
    using said DICOM communications protocol to communicate directly with said storage for prefetching at least some data of said type from the slower access part to the faster access part of said storage.

2. The method of claim 1, wherein querying by the prefetcher comprises examining a task description of said at least one task, said task description included in said DICOM modality worklist.

3. The method of claim 1, wherein querying by the prefetcher comprises examining information about said at least one modality, said information about said at least one modality included in said DICOM modality worklist.

4. The method of claim 1, wherein the at least one predetermined rule is tailored to at least one specific information consumer.

5. The method of claim 1, wherein prefetching includes: transferring data from the slower access part of the storage to the faster access part of the storage.

6. The method of claim 1, wherein prefetching includes: copying data from the slower access part of the storage to the faster access part of the storage.

7. The method of claim 1, wherein said at least one type of data comprises reference data, and wherein prefetching includes: ensuring that reference data which is deemed likely to be accessed is available in the faster access part of the storage.

8. The method of claim 1, wherein said at least one type of data comprises historical data, and wherein prefetching includes: ensuring that historical data which is deemed likely to be accessed is available in the faster access part of the storage.

9. The method of claim 8, wherein said historical data is about a specific object on which said task is to be performed.

10. The method of claim 9, wherein said object is a body part of a patient.

11. The method of claim 1, wherein said modality is an image acquisition machine.

* * * * *